United States Patent
Yoshimura

(10) Patent No.: US 11,035,756 B2
(45) Date of Patent: Jun. 15, 2021

(54) GAS ANALYZING DEVICE AND GAS ANALYZING METHOD

(71) Applicant: HORIBA, LTD., Kyoto (JP)

(72) Inventor: Tomoshi Yoshimura, Kyoto (JP)

(73) Assignee: HORIBA, LTD., Kyoto (JP)

( * ) Notice: Subject to any disclaimer, the term of this patent is extended or adjusted under 35 U.S.C. 154(b) by 170 days.

(21) Appl. No.: 16/465,751

(22) PCT Filed: Aug. 14, 2017

(86) PCT No.: PCT/JP2017/029279
§ 371 (c)(1),
(2) Date: May 31, 2019

(87) PCT Pub. No.: WO2018/105169
PCT Pub. Date: Jun. 14, 2018

(65) Prior Publication Data
US 2019/0391045 A1    Dec. 26, 2019

(30) Foreign Application Priority Data

Dec. 8, 2016 (JP) .............................. JP2016-238143

(51) Int. Cl.
*G01M 15/10* (2006.01)

(52) U.S. Cl.
CPC ................... *G01M 15/102* (2013.01)

(58) Field of Classification Search
CPC .......... G01N 33/0047; G01N 33/0024; G01N 33/0016; G01N 31/10; G01N 1/00; G01N 1/22; G01M 15/102
See application file for complete search history.

(56) References Cited

U.S. PATENT DOCUMENTS

2003/0156982 A1    8/2003  Akiyama et al.
2007/0107594 A1*   5/2007  Piccinini ................. G01N 1/22
                                                      95/52

FOREIGN PATENT DOCUMENTS

| JP | 63-308535 A | 12/1988 |
| JP | H0552755 U | 7/1993 |
| JP | 06-123682 A | 5/1994 |
| JP | 08-035950 A | 2/1996 |
| JP | 09-273991 A | 10/1997 |
| JP | 2003-315220 A | 11/2003 |

(Continued)

OTHER PUBLICATIONS

EESR dated Jul. 21, 2020 issued for European Patent Application No. 17 878 611.7, 7 pgs.

(Continued)

*Primary Examiner* — Benjamin R Schmitt
(74) *Attorney, Agent, or Firm* — Brooks Kushman P.C.

(57) ABSTRACT

In order to secure a separation ability required for an oxidation catalyst such as a non-methane cutter, and to enable a sample gas to be measured accurately, this gas analyzing device is provided with a sample gas line where a sample gas flows, an analyzer that is provided in the sample gas line and that detects the concentration of a specific component contained in the sample gas, a catalyst that is arranged upstream of the analyzer in the sample gas line and that reacts with the sample gas, and a moisture concentration adjusting unit that is arranged upstream of the catalyst in the sample gas line to adjust the moisture concentration of the sample gas.

9 Claims, 3 Drawing Sheets

(56) References Cited

FOREIGN PATENT DOCUMENTS

| | | |
|---|---|---|
| JP | 2005-055246 A | 3/2005 |
| JP | 2013-113707 A | 6/2013 |

OTHER PUBLICATIONS

International Search Report dated Oct. 10, 2017 issued for International Application No. PCT/JP2017/029279, 22 pgs.

\* cited by examiner

GAS ANALYZING DEVICE AND GAS ANALYZING METHOD

CROSS-REFERENCE TO RELATED APPLICATIONS

This application is the U.S. national phase of PCT Application No. PCT/JP2017/029279, filed Aug. 14, 2017, which claims priority to Japanese Patent Application No. 2016-238143, filed Dec. 8, 2016, which are both incorporated by reference herein in their entireties.

FIELD OF THE ART

This invention relates to a gas analyzing device and a gas analyzing method that analyzes a sample gas such as an exhaust gas discharged from, for example, an internal combustion engine.

BACKGROUND ART

This kind of the gas analyzing device measures methane or hydrocarbon other than methane contained in an exhaust gas by the use of an oxidation catalyst called as a non-methane cutter in order to remove hydrocarbon other than methane from the exhaust gas.

A separation ability of the non-methane cutter that separates the exhaust gas into methane and hydrocarbon other than methane is evaluated by transmission efficiency of methane (called as methane transmission efficiency) and transmission efficiency of, for example, ethane as being hydrocarbon other than methane (called as ethane transmission efficiency). The higher the methane transmission efficiency is, the better the separation ability is. The lower the ethane transmission efficiency is, the better the separation ability is. A concretely required level of the separation ability is the methane transmission efficiency is 85% or more and the ethane transmission efficiency is 2% or less.

The gas analyzing device described in the patent document 1 is so arranged to be able to add moisture to the non-methane cutter in order to improve the separation ability of the non-methane cutter. With this arrangement, the methane transmission ability is improved by suppressing combustion of methane in the non-methane cutter.

Meanwhile, since the ethane transmission efficiency is also improved because combustion of ethane is suppressed due to the added moisture, it is necessary to adjust the amount of moisture supplied to the non-methane cutter in order to secure the separation ability of the non-methane cutter at the required level.

However, in accordance with the patent document 1, moisture contained in the exhaust gas is not considered at all. Then if the concentration of moisture in the exhaust gas fluctuates in response to an operating state of the engine, the amount of moisture supplied to non-methane cutter increases or decreases so that the separation ability of the non-methane cutter fluctuates.

As a result of this, for the gas analyzing device described in the patent document 1, there will be a problem that it is not possible to obtain the separation ability required for non-methane cutter so that the measurement accuracy drops.

PRIOR ART DOCUMENTS

Patent Document

Patent document 1 Japanese Unexamined Patent Application Publication No. 8-35950

SUMMARY OF THE INVENTION

Problems Solved by the Invention

The present claimed invention intends to solve the above-mentioned problems and a main object is to make it possible to measure the sample gas with high accuracy while securing the separation ability required for the catalyst such as the non-methane cutter.

Means to Solve the Problems

More specifically, the gas analyzing device in accordance with this invention comprises a sample gas line where a sample gas flows, an analyzer that is arranged in the sample gas line and that detects a concentration of a specific component contained in the sample gas, a catalyst that is arranged upstream of the analyzer in the sample gas line and that reacts with the sample gas, and a moisture concentration adjusting unit that is arranged upstream of the catalyst in the sample gas line and that adjusts the concentration of moisture in the sample gas.

In dance with the gas analyzing device having this arrangement, even through the concentration of moisture in the sample gas introduced into the sample gas line fluctuates, it is possible to keep the concentration of moisture constant by adjusting the concentration of moisture in the sample gas by means of the moisture concentration adjusting unit arranged in the upstream of the catalyst in the sample gas line so that it is possible to suppress increase or decrease of the amount of moisture supplied to the catalyst.

In accordance with this arrangement, it is possible to measure the sample gas with high accuracy while securing a separation ability required for the catalyst.

If the concentration of moisture contained in the sample gas line is low, the amount of moisture supplied to the catalyst becomes insufficient and a combustion amount of methane n the catalyst increases so that there is a risk that the sufficient separation ability might not be obtained.

Then, it is preferable that the gas analyzing device comprises a moisture supplying unit to supply moisture between the moisture concentration adjusting unit and the catalyst in the sample gas line.

In accordance with this arrangement, if a predetermined amount of moisture is supplied to the sample gas whose amount of moisture is kept constant by the moisture concentration adjusting unit from the moisture supplying unit, the predetermined amount of moisture can be supplied to the catalyst so that it is possible to obtain the separation ability required for the catalyst more certainly.

As a concrete embodiment of the moisture supplying unit represented is an arrangement having a moisture supplying line connected between the moisture concentration adjusting unit and the catalyst in the sample gas line, a hydrogen introducing line that introduces hydrogen into the moisture supplying line, an oxygen introducing line that introduces oxygen into the moisture supplying line and the catalyst for generating moisture that is arranged in the moisture supplying line to generate moisture by reacting hydrogen with oxygen.

As a concrete embodiment of the moisture concentration adjusting unit represented is an arrangement wherein the concentration of moisture in the sample gas is adjusted by adjusting at least one of temperature and pressure of the sample gas.

In order to configure the moisture concentration adjusting unit with ease, it is preferable that the moisture concentration adjusting unit is a dehumidifier that reduces the concentration of moisture to a certain concentration.

If the sample gas is an exhaust gas discharged from an internal combustion engine, the concentration of moisture fluctuates in response to an operating state of the internal combustion engine so that an effect of this invention is shown more conspicuously.

In addition, a gas analyzing method in accordance with this invention is a gas analyzing method comprising steps of flowing a sample gas in a sample gas line, making the sample gas pass through a catalyst that is arranged in the sample gas line and that reacts with the sample gas, and detecting a concentration of a specific component contained in the sample gas that passes through the catalyst by the use of an analyzer, and is characterized by further comprising steps of making the sample gas pass through the moisture concentration adjusting unit prior to making the sample gas pass through the catalyst and adjusting the concentration of moisture in the sample gas.

In accordance with this gas analyzing method, it is possible to obtain the same effects as that of the above-mentioned gas analyzing device.

In order to make the separation ability of the catalyst equal both at a time of measuring the sample and at a time of correcting the analyzer, it is preferable that a correction gas to correct the analyzer is introduced into the sample gas line, and moisture is supplied to the correction gas after the correction gas passes through the moisture concentration adjusting unit and before the correction gas passes through the catalyst.

Effect of the Invention

In accordance with this invention having the above-mentioned arrangement, it is possible to measure the sample gas with high accuracy while securing a separation ability required for an oxidation catalyst such as a non-methane cutter.

DESCRIPTION OF THE REFERENCE NUMERALS

Figure 1:
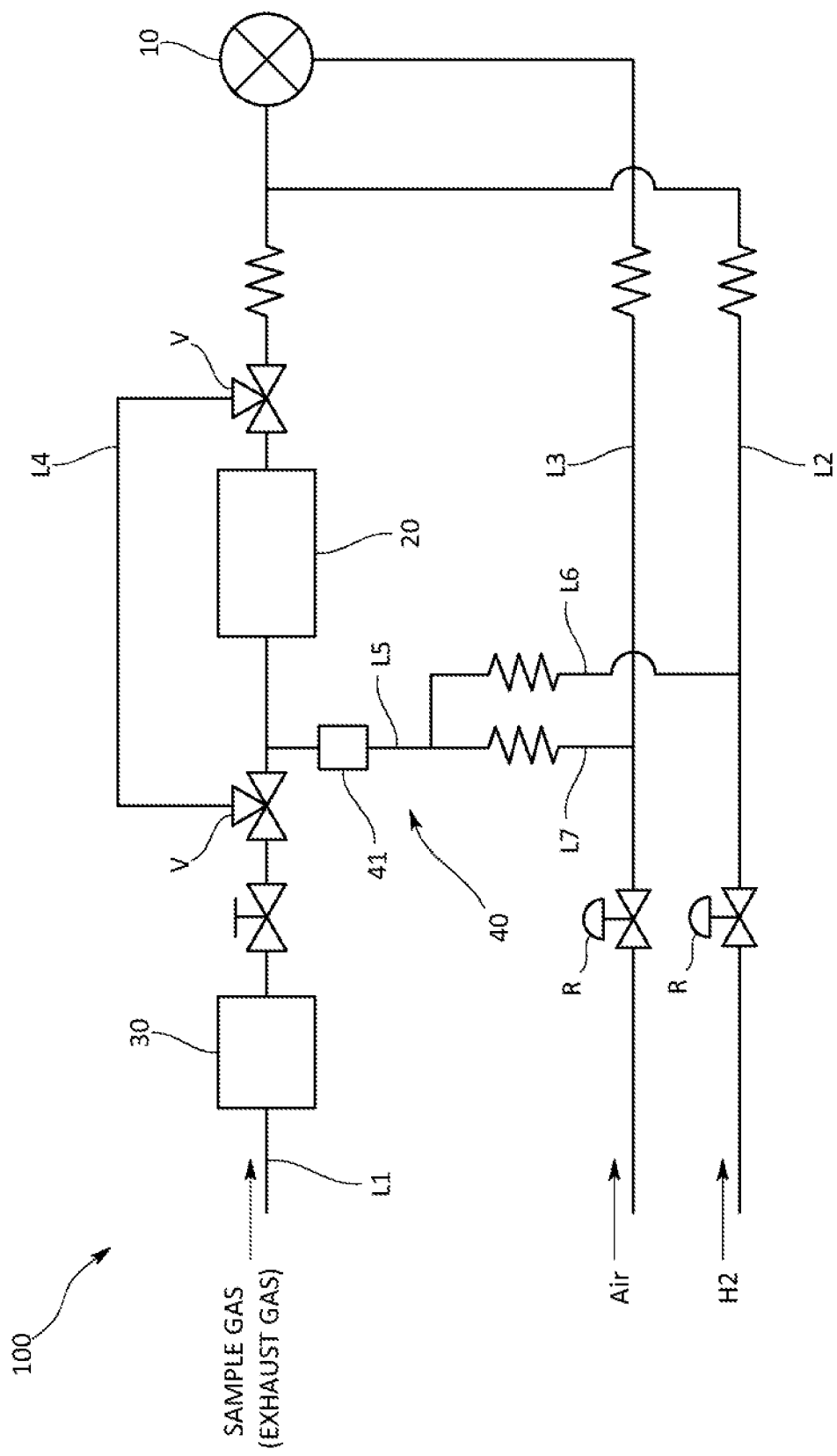
FIG. 1 is a pattern diagram showing a configuration of a gas analyzing device in accordance with this embodiment.

100 . . . gas analyzing device
L1 . . . sample gas line
L0 . . . analyzer
20 . . . oxidation catalyst
30 . . . moisture concentration adjusting unit
40 . . . moisture supplying unit
41 . . . platinum catalyst Mode for Embodying the Invention One embodiment of a gas analyzing device in accordance with this invention will be explained with reference to drawings.

The gas analyzing device 100 of this embodiment is an exhaust gas analyzing device that measures a concentration of a component contained in a sample gas such as an exhaust gas discharged from, for example, an internal combustion engine of a vehicle, and constructs an exhaust gas analyzing system together with a constant volume sample device (CVS) that samples a mixed gas that is made by diluting, for example, the exhaust gas with dilution air at a constant flow rate. The exhaust gas analyzing system may be a dilution sampling system that dilutes the exhaust gas and measures a concentration of the component, or a direct sampling system that measures the concentration of the component without diluting the exhaust gas.

Concretely, the gas analyzing device 100 comprises, as shown in FIG. 1, a sample gas line L1 where the exhaust gas as being the sample gas flows and an analyzer 10 that is arranged in the sample gas line L1 and that measures a concentration of a component as being an object to be measured contained in the sample gas.

The analyzer 10 measures hydrocarbon (HC) as being an organic compound as the object to be measured, and has a flame ionization detector (FID) that uses a flame ionization analyzing method and measures the concentration of total hydrocarbon (THC) contained in the sample gas.

Concretely, a gas line L2 for analysis through which a hydrogen gas as being a gas for analysis is supplied and a combustion aid gas line L3 through which air as being a combustion aid gas is supplied are connected to the analyzer 10, and the analyzer 10 is so configured that the gas for analysis and the combustion aid gas are mixed into the collected sample gas at a constant ratio and the mixed gas is introduced into hydrogen flame and the concentration of hydrocarbon (HC) can be continuously measured based on ion currents generated by ionizing hydrocarbon at a time of combustion.

As shown in FIG. 1, the gas analyzing device 100 of this embodiment is arranged upstream side of the analyzer 10 in the sample gas line L1 and comprises an oxidation catalyst 20 to remove hydrocarbon (a component to be removed) other than methane from the sample gas.

Furthermore, in this embodiment, a bifurcated line L4 that bifurcates upstream side of the oxidation catalyst 20 and joins downstream thereof and a switch valve (V) such as a three-way valve to flow the sample gas in the bifurcated line L4 or the oxidation catalyst 20 alternatively.

In accordance with this arrangement, it is possible to measure the concentration of the total hydrocarbon (THC) by flowing the sample gas in the bifurcated line L4, and it is possible to measure the concentration of methane contained in the sample gas by flowing the sample gas in the oxidation catalyst 20 so that the concentration of non-methane hydrocarbon (NMHC) contained in the sample gas can be calculated based on the difference between the concentration of total hydrocarbon and the concentration of methane.

The above-mentioned oxidation catalyst 20 is a metal catalyst called as, so called, a non-methane cutter, and concretely contains manganese dioxide (IV) or copper oxide (II) and is used within a specified temperature range such as, for example, 600 K or more. A separation ability of this non-methane cuter is evaluated by, for example, penetration efficiency of methane and the penetration efficiency of ethane as being hydrocarbon other than methane, however, the penetration efficiency fluctuates in response to the temperature of methane cuter. As a result of this, the separation ability also fluctuates in response to the temperature of the non-methane cutter.

If moisture is supplied to the non-methane cutter, since methane and hydrocarbon other than methane become difficult to be burned and easily penetrate the non-methane cutter, the penetration efficiency increases. At this time, since a ratio of increasing the penetration efficiency of methane is bigger than the ratio of increasing the penetration efficiency of hydrocarbon other than methane, if an amount of moisture is supplied to the non-methane cutter appropriately within the above-mentioned specified temperature range, it is possible to increase the penetration efficiency of methane while the penetration efficiency of hydrocarbon other than methane is kept low. More specifically, it is possible to increase the separation ability of the non-methane cutter by appropriately adjusting the amount of moisture supplied to the non-methane cutter (for example, the penetration efficiency of methane is 85% or more and the penetration efficiency of ethane is 2% or less).

And then, as shown in FIG. 1, the gas analyzing device 100 of this embodiment is arranged upstream of the oxidation catalyst 20 in the sample gas line L1 and further comprises a moisture concentration adjusting unit 30 that adjusts the concentration of moisture in the sample gas.

The moisture concentration adjusting unit 30 is so configured to keep the concentration of moisture constant by changing the temperature of the sample gas, and reduces the concentration of moisture contained in the sample gas to a previously determined set concentration. The moisture concentration adjusting unit 30 makes use of a dehumidifier that dehumidifies the sample gas by cooling the sample gas, and the dehumidifier is of a compressor type using, for example, a compressor. The set concentration can be changed appropriately in accordance with a specification or the like.

In addition, the moisture concentration adjusting, unit 30 may adjust the concentration of moisture by changing a pressure of the sample gas, or may adjust the concentration of moisture by changing both the temperature and the pressure of the sample gas.

Furthermore, as shown in FIG. 1, the gas analyzing device 100 of this embodiment comprises a moisture supplying unit 40 that supplies moisture between the moisture concentration adjusting unit 30 and the oxidation catalyst 20 in the sample gas line L1.

The moisture supplying unit 40 comprises a moisture supplying line L5 connected between the moisture concentration adjusting unit 30 and the oxidation catalyst 20 in the sample gas line L1, a hydrogen introducing line L6 that introduces hydrogen into the moisture supplying line L5, an oxygen introducing line L7 that introduces oxygen into the moisture supplying line L5 and a platinum catalyst 41 as being a catalyst for generating moisture that is arranged in the moisture supplying line L5 and that generates moisture by reacting hydrogen with oxygen.

The hydrogen introducing line L6 is a line where a gas comprising hydrogen alone or a gas containing a predetermined concentration of hydrogen flows, and a part of the hydrogen introducing line L6 is also used as the above-described gas line for analysis L2.

The oxygen introducing line L7 is a line that introduces a gas comprising oxygen alone or a gas containing a predetermined concentration of oxygen. The oxygen introducing line L7 is a line where air flows, and a part of the above-described oxygen introducing line L7 is also used as the combustion aid gas line L3.

Each of the hydrogen introducing line L6 and the oxygen introducing line L7 is provided with a regulator (R) respectively, and the regulator (R) makes it possible to control the moisture amount to be generated, more specifically the moisture amount supplied to the sample gas line L1 to be a predetermined amount by adjusting the flow rate of the hydrogen or oxygen supplied to the catalyst for generating the moisture. The moisture supplying unit 40 of this embodiment supplies the moisture of 1~2 vol % to the sample gas line L1.

In this embodiment, in case of correcting the analyzer 10, a correction gas containing methane whose concentration is known is introduced into the sample gas line L1. With this arrangement, it is possible to correct the analyzer 10 as needed by comparing the known concentration of methane contained in the correction gas with the measured concentration of methane obtained by the use of the analyzer 10. The correction gas may be a gas containing ethane or propane whose concentration is known.

The correction gas used in this embodiment is a gas whose amount of moisture is less than that of the exhaust gas as being the sample gas. As a result of this, if the moisture concentration adjusting unit 30 is not provided, the amount of moisture supplied to the non-methane cutter differs between at the time of correction and at the time of analysis. Then, the separation ability of the non-methane cutter differs between at the time of correction and at the time of analysis, resulting in drop of the analysis accuracy.

Then, in this embodiment, the correction gas is made to pass through the moisture concentration adjusting unit 30 by introducing the correction gas used at the time of correction into the sample gas line L1.

Figure 2:
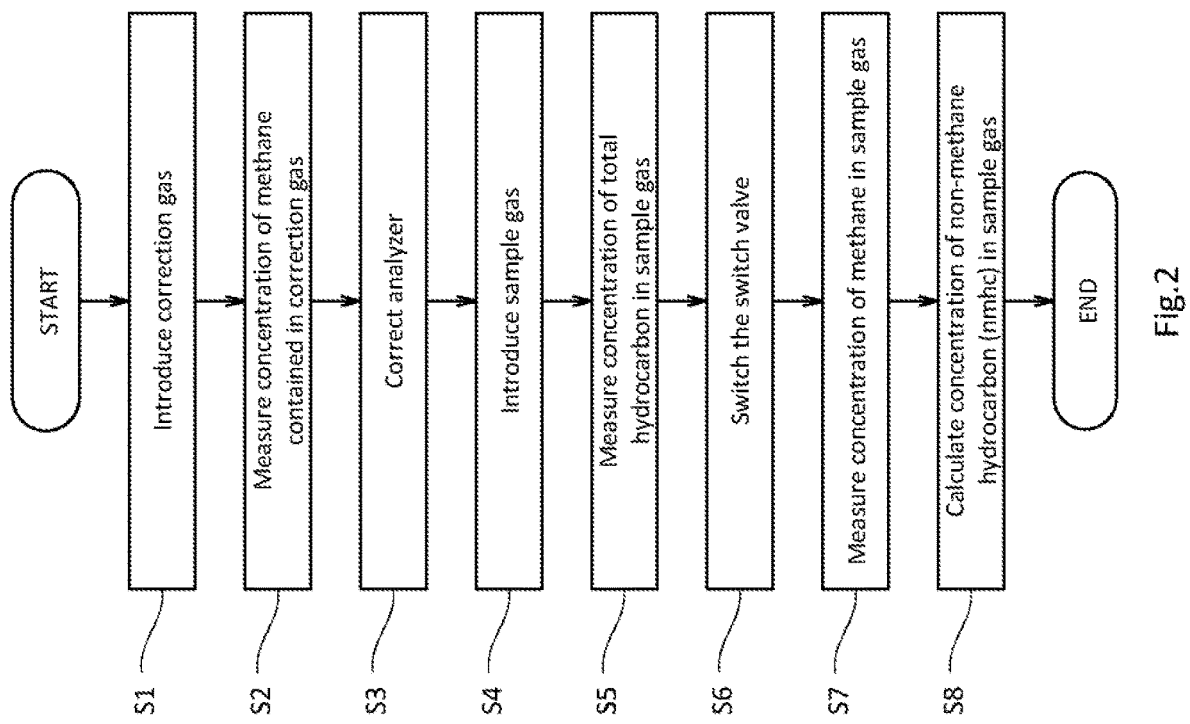
FIG. 2 is a view showing a flow chart of an operation of the gas analyzing device in accordance with this embodiment.

A gas analyzing method in accordance with this embodiment will be explained with reference to a flow chart in FIG. 2.

First, the correction gas to correct the analyzer 10 is introduced into the sample gas line L1 (S1). A switch valve (V) at this time is set in a state wherein the correction gas flows in the non-methane cutter.

With this process, after a predetermined amount of moisture is supplied to the correction gas from the moisture supplying unit 40, the correction gas flows in the non-methane cutter so that hydrocarbon other than methane is removed. Then, the concentration of methane contained in the correction gas is measured by the analyzer 10 (S2).

Based on the calculated result, a user compares the measured concentration of methane obtained by the analyzer 10 with the known concentration of methane actually contained in the correction gas and corrects the analyzer 10 as necessary (S3).

Subsequently, the exhaust gas as being the sample gas is introduced into the sample gas line L1 (S4). The switch valve (V) at this time is set in a state a wherein the correction gas flows in the bifurcated line L4.

With this process, the sample gas is introduced into the analyzer 10 without passing through the non-methane cutter, and the concentration of total hydrocarbon contained in the sample gas is measured by the analyzer 10 (S5).

Next, the switch valve (V) is switched so that the sample gas flows in the non-methane cutter (S6).

With this process, after a predetermined amount of moisture is supplied to the sample gas from the moisture supplying unit 40, the sample gas flows in the non-methane cutter so that hydrocarbon other than methane is removed. Then, the concentration of methane contained in the sample gas is measured by the analyzer 10 (S7).

Then an arithmetic processing unit, not shown in drawings, comprised by the analyzer 10 or provided separately from the analyzer 10 calculates the concentration of non-methane hydrocarbon (NMHC) contained in the sample gas based on the difference between the concentration of total hydrocarbon and the concentration of methane (S8).

In accordance with the gas analyzing device 100 having the above-mentioned arrangement, since the concentration of moisture contained in the sample gas is reduced to a certain concentration by the use of the dehumidifier and the predetermined amount of moisture is supplied to the sample gas, it is possible to keep the amount of the moisture supplied to the oxidation catalyst 20 constant even though the concentration of moisture in the exhaust gas fluctuates in response to the operating state of the internal combustion engine.

In accordance with this, it is possible to control fluctuation of the separation ability of the oxidation catalyst 20 so that the analysis accuracy can be improved.

In addition, since the correction gas is introduced into the sample gas line L1 and the predetermined amount of moisture is supplied while the correction gas passes through the moisture concentration adjusting unit 30, it is possible to make the separation ability of the oxidation catalyst 20 at a time of measuring the sample gas equal to that at a time of correcting the analyzer 10 so that the analysis accuracy can be further improved.

This invention is not limited to the above-mentioned embodiment.

Figure 3:
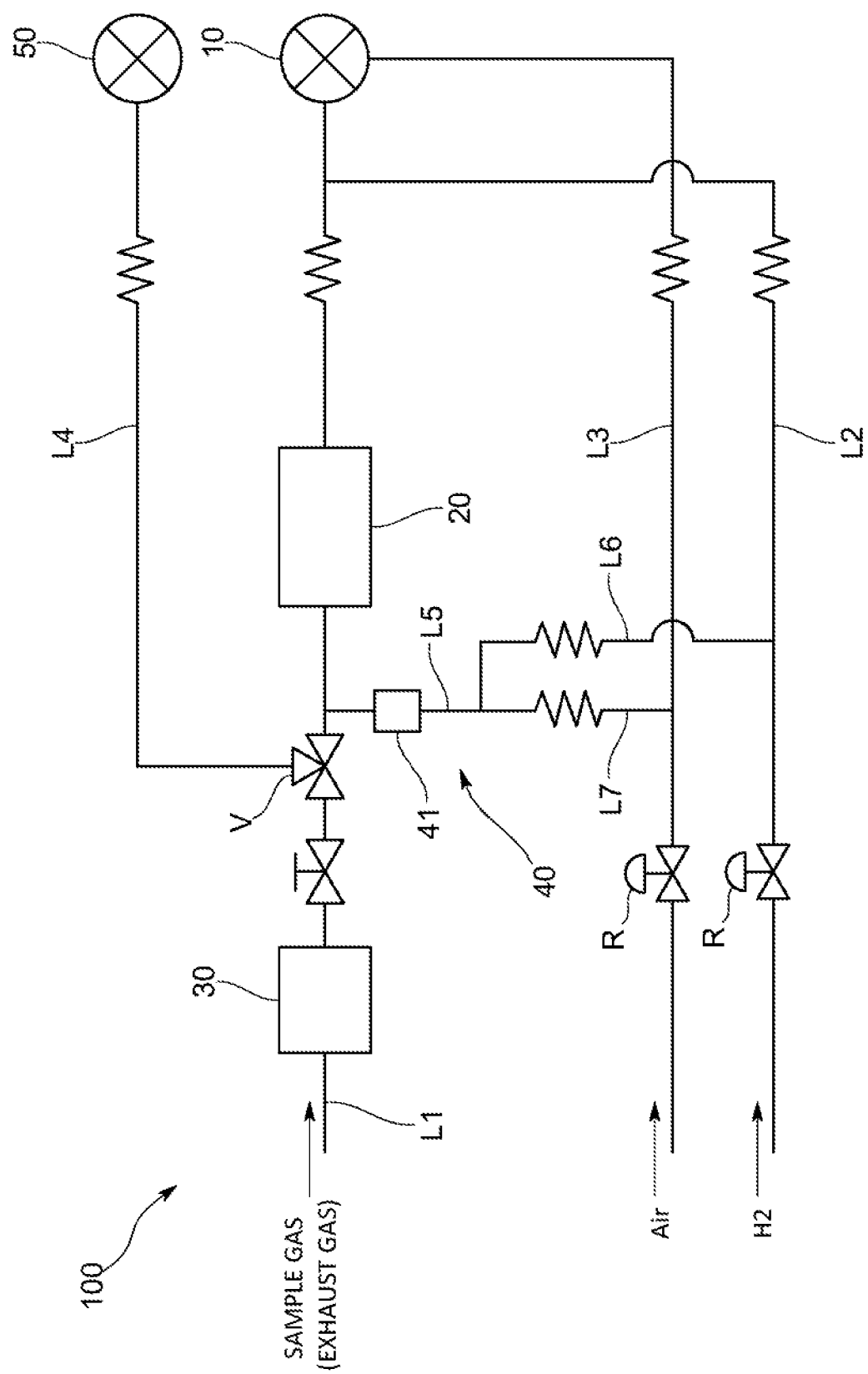
FIG. 3 is a pattern diagram showing a configuration of a gas analyzing device in accordance with a modified embodiment.

For example, as shown in FIG. 3, the bifurcated line L4 that bifurcates from the upstream side of the non-methane cutter may be connected to a second analyzer 50 (THC meter) that analyzes, for example, total hydrocarbon without joining the downstream side of the non-methane cutter. In this case, the analyzer 10 may be a $CH_4$ meter that measures the concentration of methane.

Similar to this embodiment, these THC meter or the $CH_4$ meter has an FID detector.

In accordance with this arrangement, it is possible to measure the concentration of total hydrocarbon in the step (S5) in the above-mentioned embodiment and to measure the concentration of methane in the step (S7) in parallel.

In addition, since moisture contained in the sample gas is removed by the moisture concentration adjusting unit 30, the concentration of methane or hydrocarbon other than methane contained in the sample gas changes so that a moisture partial pressure correcting unit may be provided for an arithmetic processing unit comprised by the analyzer 10 or separately arranged from the analyzer 10.

Concretely, as the moisture partial pressure correcting unit represented is an arrangement to obtain a removed moisture amount data indicating the amount of moisture in the sample gas from which moisture is removed by the moisture concentration adjusting unit 30 and to correct the concentration of methane or the concentration of total hydrocarbon in response to the moisture amount.

Furthermore, the moisture concentration adjusting unit 30 may be a desiccant dehumidifier that makes use of a drying agent such as porous mineral.

In addition, the moisture concentration adjusting unit 30 may have an arrangement wherein the introduced sample gas passes through liquid stored in a tank. More concretely, if the liquid in the tank is provided with a bubbling treatment while the liquid is kept at a certain temperature, the moisture contained in the sample gas becomes in a state of saturation so that the amount of moisture in the sample gas can be kept constant. With this arrangement, if the amount of moisture in the sample gas can be adjusted at a desired amount, it is possible to omit the moisture supplying unit 40 in the above-mentioned embodiment.

In addition, the concentration of methane is measured after the concentration of total hydrocarbon contained in the sample gas is measured in the above-mentioned embodiment, however, the concentration of the total hydrocarbon may be measured after the concentration of methane is measured.

In case that the concentration of moisture contained in the correction gas is extremely low, the concentration of the correction gas that passes through the moisture concentration adjusting unit 30 remains to be lower than the concentration set by the concentration adjusting unit 30, and a difference is caused between the amount of moisture supplied to the non-methane cutter at a time of correction and that at a time analysis.

Then, in case of correcting the analyzer 10 by the use of the correction gas, the correction gas may be made to flow in the moisture concentration adjusting unit 30 after the correction gas is humidified.

In accordance with this arrangement, if the correction gas is made to flow in the moisture concentration adjusting unit 30 after the concentration of moisture contained in the correction gas is made to be more than or equal to the set concentration of the moisture concentration adjusting unit 30, it is possible to make the concentration of moisture contained in the correction gas that passes through the moisture concentration adjusting unit 30 at the above-mentioned set concentration and to reduce a difference between the amount of moisture supplied to the non-methane cutter at the time of correction and that at the time of analysis as much as possible.

In addition, the analyzer 10 may make use of infrared absorption such as a CO meter or a $CO_2$ meter.

Furthermore, the gas analyzing device 100 in accordance with this invention can be used as an onboard analyzer loaded on a vehicle. In case of using the gas analyzing device 100 as the onboard analyzer, since there is a limit on electric power supply of the moisture concentration adjusting unit 30, electric power consumption may be suppressed by raising the set temperature of the moisture concentration adjusting unit 30 or the above-mentioned desiccant dehumidifier may be used as the moisture concentration adjusting unit 30.

In addition, the gas analyzing device 100 in accordance with this invention can be used also as a catalyst evaluation device.

Furthermore, the sample gas may be not only the exhaust gas from the internal combustion engine but also various kinds of gas such as a gas introduced into or discharged from a combustion engine such as a boiler or a chemical reactor.

This invention is not limited to the above-mentioned embodiment, and it is a matter of course that various modifications may be made without departing from the spirit of this invention.

INDUSTRIAL APPLICABILITY

If the gas analyzing device in accordance with this invention is used, it is possible to measure the sample gas with high accuracy by securing a separation ability required for an oxidation catalyst such as a non-methane cutter.

The invention claimed is:
1. A gas analyzing device comprising:
a sample gas line where a sample gas flows;
an analyzer that is arranged in the sample gas line and that detects a concentration of a specific component contained in the sample gas;

a catalyst that is arranged upstream of the analyzer in the sample gas line and that reacts with the sample gas;

a moisture concentration adjusting unit that is arranged upstream of the catalyst in the sample gas line and that adjusts a concentration of moisture in the sample gas; and a moisture supplying unit that supplies moisture to the sample gas in the sample gas line between the moisture concentration adjusting unit and the catalyst.

2. The gas analyzing device described in claim 1, wherein the moisture supplying unit comprises a moisture supplying line connected between the moisture concentration adjusting unit and the catalyst in the sample gas line, a hydrogen introducing line that introduces hydrogen into the moisture supplying line, an oxygen introducing line that introduces oxygen into the moisture supplying line, and a catalyst for generating moisture that is arranged in the moisture supplying line to generate moisture by reacting hydrogen with oxygen.

3. The gas analyzing device described in claim 1, wherein the moisture concentration adjusting unit adjusts the concentration of moisture in the sample gas by adjusting at least one of temperature and pressure of the sample gas.

4. The gas analyzing device described in claim 1, wherein the moisture concentration adjusting unit is a dehumidifier that reduces the concentration of moisture to a certain concentration.

5. The gas analyzing device described in claim 1, wherein the sample gas is an exhaust gas discharged from an internal combustion engine.

6. A gas analyzing method; comprising:

flowing a sample gas in a sample gas line;

making the sample gas pass through a moisture concentration adjusting unit that is arranged in the sample gas line;

adjusting a concentration of moisture in the sample gas by use of the moisture concentration adjusting unit;

making the sample gas pass through a catalyst that is arranged in the sample gas line and that reacts with the sample gas;

supplying moisture to the sample gas after the sample gas passes through the moisture concentration adjusting unit and before the sample gas passes through the catalyst by use of a moisture supplying unit; and detecting a concentration of a specific component contained in the sample gas that passes through the catalyst by use of an analyzer that is arranged in the sample gas line.

7. The gas analyzing method described in claim 6, further comprising introducing a correction gas to correct the analyzer into the sample gas line, and supplying moisture to the correction gas after the correction gas passes through the moisture concentration adjusting unit and before the correction gas passes through the catalyst.

8. The gas analyzing method described in claim 7, further comprising making the correction gas pass through the moisture concentration adjusting unit after the correction gas is humidified.

9. A gas analyzing device comprising:

a sample gas line where a sample gas flows;

an analyzer that is arranged in the sample gas line and that detects a concentration of a specific component contained in the sample gas;

a catalyst that is arranged upstream of the analyzer in the sample gas line and that reacts with the sample gas, and a moisture concentration adjusting unit that is arranged upstream of the catalyst in the sample gas line and that adjusts a concentration of moisture in the sample gas, wherein the moisture concentration adjusting unit comprises a tank in which liquid is stored and which is provided with a bubbling treatment, and wherein the tank is arranged such that the sample gas passes through the tank.

* * * * *